(12) United States Patent
Zhou et al.

(10) Patent No.: US 9,962,668 B2
(45) Date of Patent: May 8, 2018

(54) SHAKING DEVICE FOR FULLY-AUTOMATIC INSTANT CHECK METER

(71) Applicant: HANGZHOU JOINSTAR BIOMEDICAL TECHNOLOGY CO., LTD., Hangzhou, Zhejiang Province (CN)

(72) Inventors: Xuyi Zhou, Hangzhou (CN); Longbin Hong, Hangzhou (CN); Wenjie Xu, Hangzhou (CN); Xiaodong Chen, Hangzhou (CN); Songbing Zhou, Hangzhou (CN); Guojin Shen, Hangzhou (CN); Rui Hu, Hangzhou (CN)

(73) Assignee: HANGZHOU JOINSTAR BIOMEDICAL TECHNOLOGY CO., LTD., Hangzhou, Zhejiang Province (CN)

(*) Notice: Subject to any disclaimer, the term of this patent is extended or adjusted under 35 U.S.C. 154(b) by 0 days. days.

(21) Appl. No.: 15/101,199

(22) PCT Filed: Dec. 25, 2014

(86) PCT No.: PCT/CN2014/094948
§ 371 (c)(1),
(2) Date: Jun. 2, 2016

(87) PCT Pub. No.: WO2015/196773
PCT Pub. Date: Jul. 2, 2015

(65) Prior Publication Data
US 2016/0303528 A1    Oct. 20, 2016

(30) Foreign Application Priority Data

Dec. 26, 2013  (CN) .................... 2013 2 0866292 U

(51) Int. Cl.
*B01F 11/00* (2006.01)
*G01N 35/00* (2006.01)
(Continued)

(52) U.S. Cl.
CPC ...... *B01F 11/0025* (2013.01); *B01F 11/0005* (2013.01); *B01F 11/0022* (2013.01);
(Continued)

(58) Field of Classification Search
CPC .............. B01F 11/0025; B01F 11/0022; B01F 2215/0037; B01F 11/0005; G01N 1/38;
(Continued)

(56) References Cited

U.S. PATENT DOCUMENTS 6,808,304 B2 * 10/2004 Gebrian .............. B01F 11/0022
366/110
8,016,218 B1 * 9/2011 Friedman ............ B01F 11/0017
241/175

(Continued)

FOREIGN PATENT DOCUMENTS

CN    101379403 A    3/2009
CN    201497691 U    6/2010
(Continued)

*Primary Examiner* — Charles Cooley
(74) *Attorney, Agent, or Firm* — Muncy, Geissler, Olds & Lowe, P.C.

(57) ABSTRACT

A shaking device for a fully-automatic instant check meter, which is used for shaking blood in a test tube uniformly. The shaking device comprises a frame body, a barcode printer, a first bracket, a second bracket, a rotating mechanism, a vacuum blood vessel shaking mechanism and a peripheral blood vessel shaking mechanism, wherein a first sliding rail, a first motor and a second motor are provided on the frame body; the rotating mechanism is connected to the first sliding rail in a sliding manner via a first sliding block and is connected to the first motor via a first synchronous belt; the (Continued)

vacuum blood vessel shaking mechanism is connected to the first sliding rail in a sliding manner via a second sliding block and is connected to a second motor via a second synchronous belt; the peripheral vessel shaking mechanism is arranged below the vacuum blood vessel shaking mechanism; and the barcode printer is arranged at one side of the frame body. The shaking device has a simple structure and a good shaking effect, and is safe and reliable.

6 Claims, 4 Drawing Sheets

(51) Int. Cl.
  *B06B 1/10* (2006.01)
  *G01N 1/38* (2006.01)
  *G01N 33/49* (2006.01)

(52) U.S. Cl.
  CPC ............... *B06B 1/10* (2013.01); *G01N 1/38* (2013.01); *G01N 33/49* (2013.01); *G01N 35/0099* (2013.01); *B01F 2215/0037* (2013.01); *G01N 2001/386* (2013.01); *G01N 2035/00524* (2013.01)

(58) Field of Classification Search
  CPC ............... G01N 33/49; G01N 35/0099; G01N 2001/386; G01N 2035/00524; B06B 1/10
  See application file for complete search history.

(56) References Cited

U.S. PATENT DOCUMENTS

| | | | | |
|---|---|---|---|---|
| 8,834,010 | B2* | 9/2014 | Boquet | B01F 11/0008 366/110 |
| 9,802,170 | B2* | 10/2017 | Endo | B01F 11/0005 |
| 2004/0042339 | A1* | 3/2004 | Gebrian | B01F 11/0022 366/208 |
| 2016/0299166 | A1* | 10/2016 | Zhou | G01N 35/04 |
| 2016/0303528 | A1* | 10/2016 | Zhou | G01N 35/0099 |

FOREIGN PATENT DOCUMENTS

| | | |
|---|---|---|
| CN | 201903549 U | 7/2011 |
| CN | 102147406 A | 8/2011 |
| CN | 201965137 U | 9/2011 |
| CN | 203630149 U | 6/2014 |
| WO | WO 2013/016034 A1 | 1/2013 |

\* cited by examiner

SHAKING DEVICE FOR FULLY-AUTOMATIC INSTANT CHECK METER

FIELD OF THE INVENTION

The utility model relates to the technical field of medical testing apparatus, in particular, to a shaking device for a fully-automatic instant check meter.

BACKGROUND OF THE INVENTION

Currently there are many medical testing apparatuses available on the markets, with high degree of automation and high detection capacity; but they require complicated sample pre-treatment processes and a long time of detection cycle, especially the early stage processing of blood in the test tube, such as shaking; the large fully-automatic test apparatus has a complicated structure, and it is inconvenient for operators to carry out operation, moreover, it costs much. The existing POCT (Point-Of-Care Testing) products can achieve a miniature, immediate and simple bedside testing, but POCT has a common feature—single detection; if there are many clinical specimens in batches or the number of specimens for the same test item in the emergency testing is large, the single, small POCT testing instruments can not meet their requirements; moreover, their degree of automation is not high, requiring manual operation, and the expense is high; in addition, the consistency of test results is low.

SUMMARY OF THE INVENTION

This utility model provides a shaking device for a fully-automatic instant check meter. The shaking device has a simple structure and a good shaking effect, and is safe and reliable.

The utility model is achieved through the following technical solutions:

A shaking device for a fully-automatic instant check meter is used for shaking blood in a test tube uniformly, comprising a frame body, a barcode printer, a first bracket, a second bracket, a rotating mechanism, a vacuum blood vessel shaking mechanism and a peripheral blood vessel shaking mechanism, wherein a first sliding rail, a first motor and a second motor are provided on the frame body; the rotating mechanism is connected to the first sliding rail in a sliding manner via a first sliding block and is connected to the first motor via a first synchronous belt; the vacuum blood vessel shaking mechanism is connected to the first sliding rail in a sliding manner via a second sliding block and is connected to a second motor via a second synchronous belt; the peripheral vessel shaking mechanism is arranged below the vacuum blood vessel shaking mechanism; and the barcode printer is arranged at one side of the frame body.

The rotating mechanism comprises a first bracket and a first DC motor. The first bracket is fixed to the first sliding block by screws, and the first DC motor is fixed on the first bracket with the output end downwards. A rotating friction head is arranged on the output end.

The vacuum blood vessel shaking mechanism comprises a second bracket, a guide block and a gripper. The guide block is fixed on the frame body and located above the first sliding rail, the second bracket is fixed to the second sliding block by screws. A check block is provided on one side of the second bracket, the gripper is connected to the check block via a rotating shaft. The check block rotates under the guidance of the guide block and drives the gripper to rotate.

The gripper comprises a second DC motor, a left grab block, a right grab block and a first lead screw. The second DC motor is fixed on the second bracket. The output end of the second DC motor is provided with the first driving wheel, and one end of the first lead screw is provided with the first driven wheel. The first driving wheel is meshed with the first driven wheel, and the left grab block and right grab block are set on the first lead screw.

The peripheral blood vessel shaking mechanism comprises an installation platform, a third DC motor, a second lead screw, a fixed block, a brushless motor and a fixing piece. The installation platform is provided with a second sliding rail, the fixed block is connected with the second sliding rail in a sliding manner. The third DC motor is fixed on the installation platform, and the output end of the third DC motor is provided with a second driving wheel. One end of the second lead screw is provided with a second driven wheel. The second driving wheel is meshed with the second driven wheel. The fixed block is connected with the second lead screw. The fixing piece is provided with a brushless motor. The fixing piece is connected with the fixed block via rubber feet. The output end of the brushless motor is provided with an eccentric block. A shaking block is arranged above the fixing piece, and the shaking block is provided with a jack.

The end of check block in contact with the guide block is provided with bearings.

The utility model can achieve the following beneficial effects:

The shaking device for a fully-automatic instant check meter in the utility model can be used for shaking vacuum blood vessels and peripheral blood vessels. Before use of the barcode printer, the barcodes on the sample rack are firstly scanned to confirm the type of blood vessels, and then the barcodes on the blood vessels are scanned, to record the barcode information. If it is vacuum blood vessel and when the barcode of blood vessel cannot be scanned, the rotating friction head moved downwards to compress the vacuum blood vessels for rotary operation driven by the first motor. The vacuum blood vessel shaking mechanism is used for shaking the blood in the vacuum blood vessel, and the gripper is used for gripping various kinds of vessels. The peripheral blood vessel shaking mechanism is used for shaking the blood in the peripheral blood vessel; firstly gripping the peripheral blood vessels from the sample rack by the gripper, and then inserting the peripheral blood vessel on the jack of the shaking block. The shaking block is driven by the brushless motor to shake, and thus shaking the blood in the peripheral blood vessel.

BRIEF DESCRIPTION OF TILE DRAWINGS

The utility model is further described in combination with the drawings.

1, frame body; 2, barcode printer; 3, first bracket; 4, second bracket; 5, first sliding rail; 6, first motor; 7, second motor; 8, first sliding block; 9, first synchronous belt; 10, second sliding block; 11, second synchronous belt; 12, first DC motor; 13, rotating friction head; 14, guide block; 15, check block; 16, rotating shaft; 17, second DC motor; 18, left grab block; 19, right grab block; 20, first lead screw; 21, first driving wheel; 22, first driven wheel; 23, installation platform; 24, third DC motor; 25, second lead screw; 26, fixed block; 27, brushless motor; 28, fixing piece; 29, second sliding rail; 30, second driving wheel; 31, second driven wheel; 32, rubber feet; 33, eccentric block; 34, shaking block; 35, jack; 36, bearing; 40, vacuum blood vessel; 50, peripheral blood vessel.

DETAILED DESCRIPTION OF THE EMBODIMENTS

The utility model is further described in details in combination with drawings and embodiments.

Figure 1:
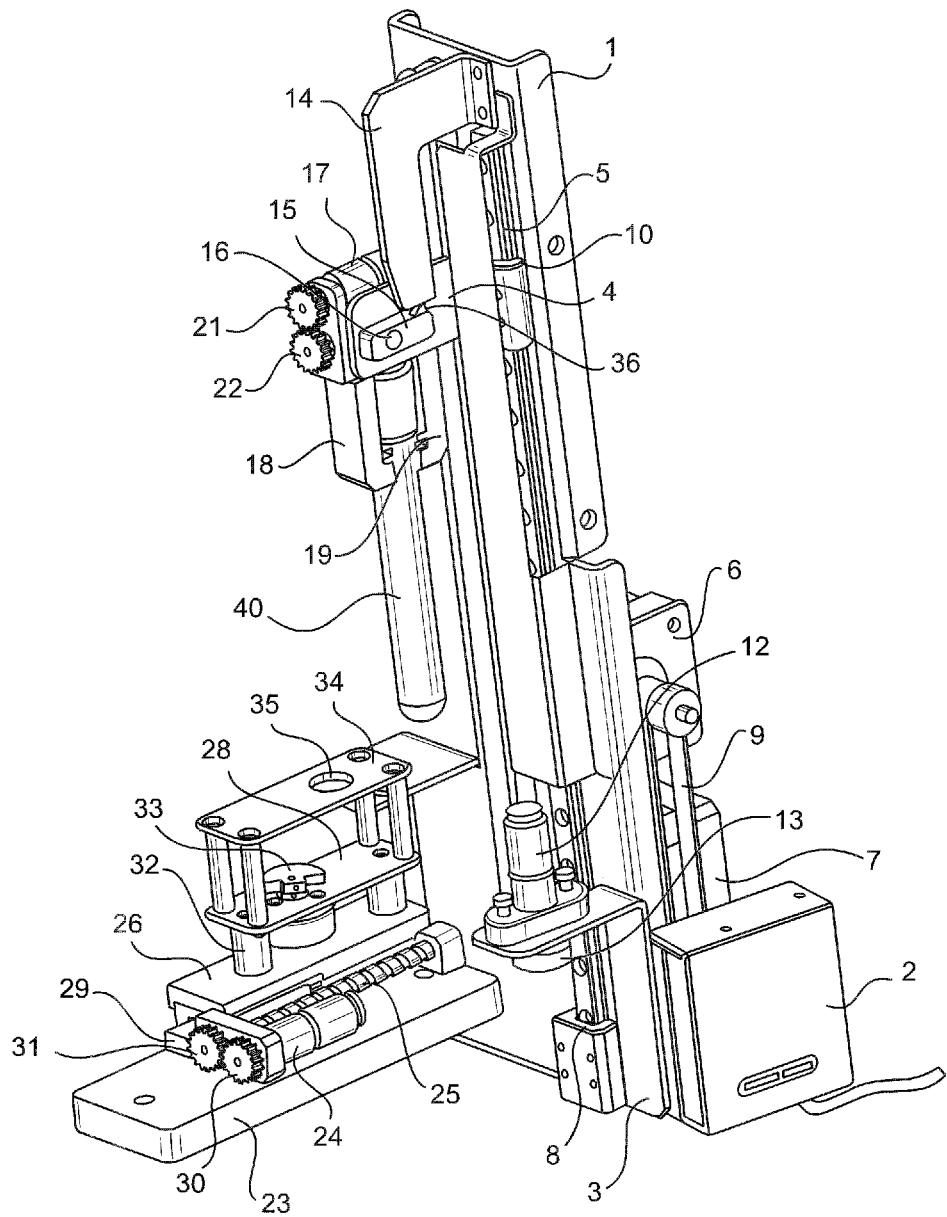
FIG. 1 is a schematic diagram of the shaking device for a fully-automatic instant check meter for shaking vacuum blood vessels under the first state.
Figure 2:
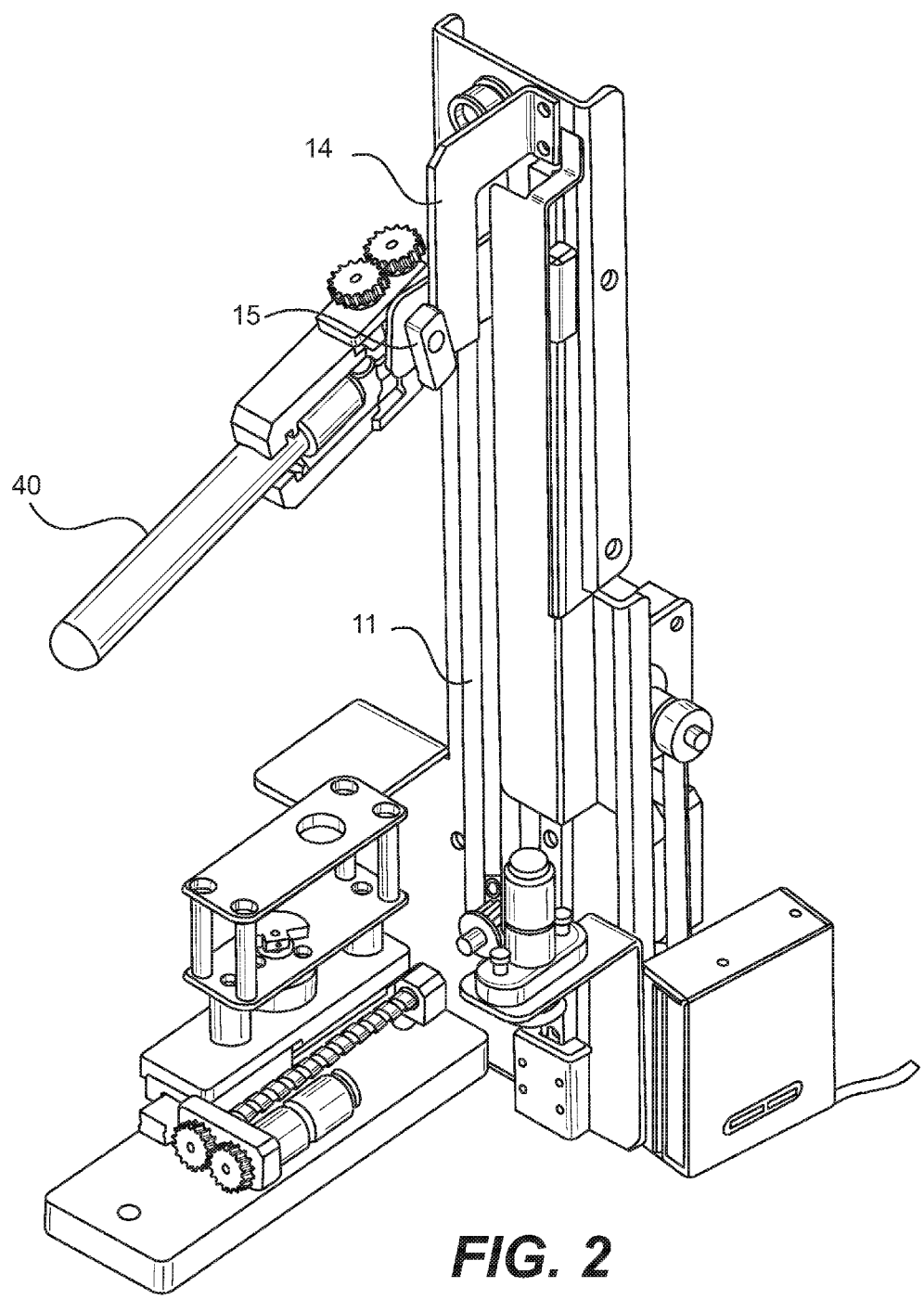
FIG. 2 is a schematic diagram of the shaking device for a fully-automatic instant check meter for shaking vacuum blood vessels under the second state.
Figure 3:
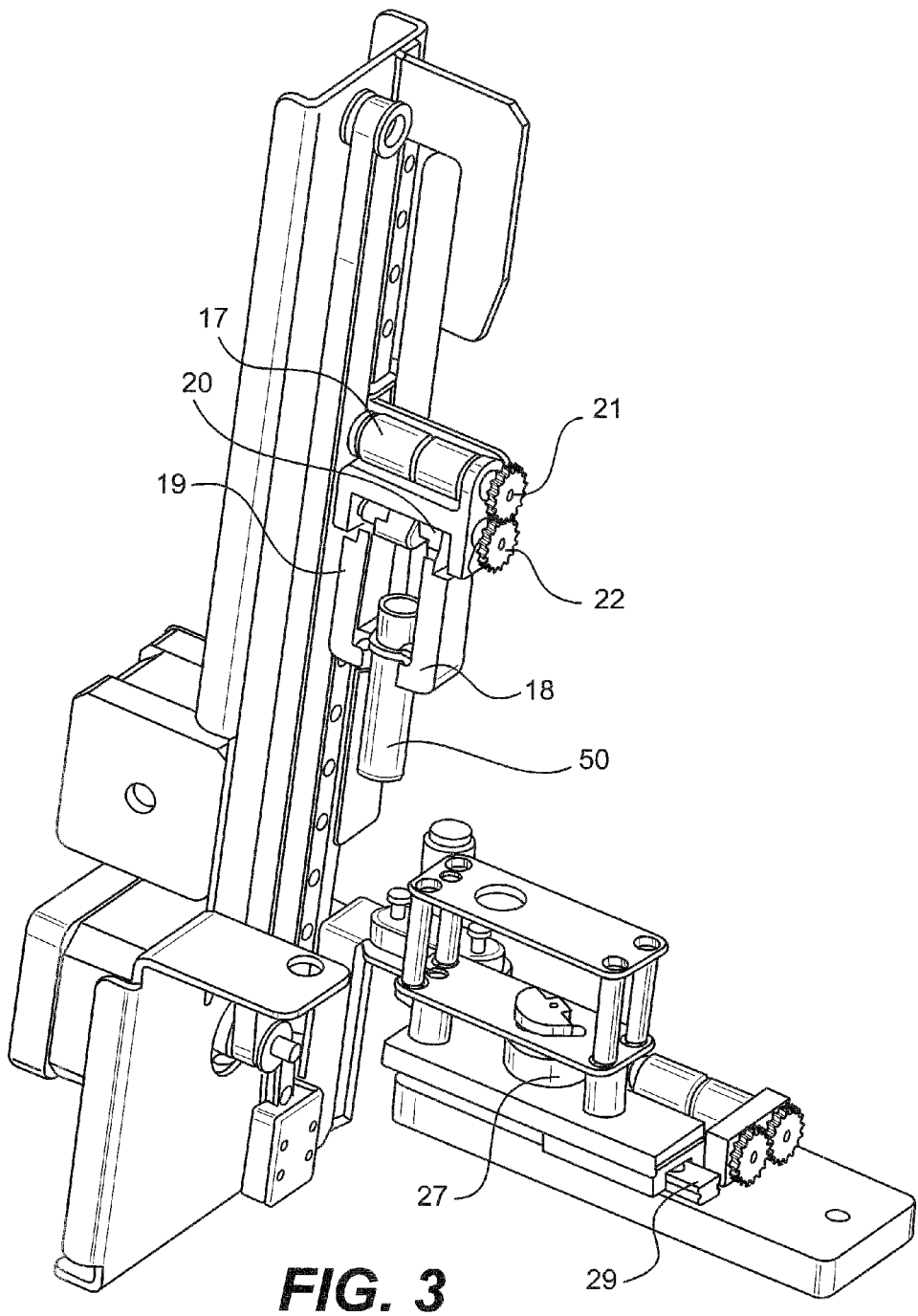
FIG. 3 is a schematic diagram of the shaking device for a fully-automatic instant check meter for shaking peripheral blood vessels under the first state.
Figure 4:
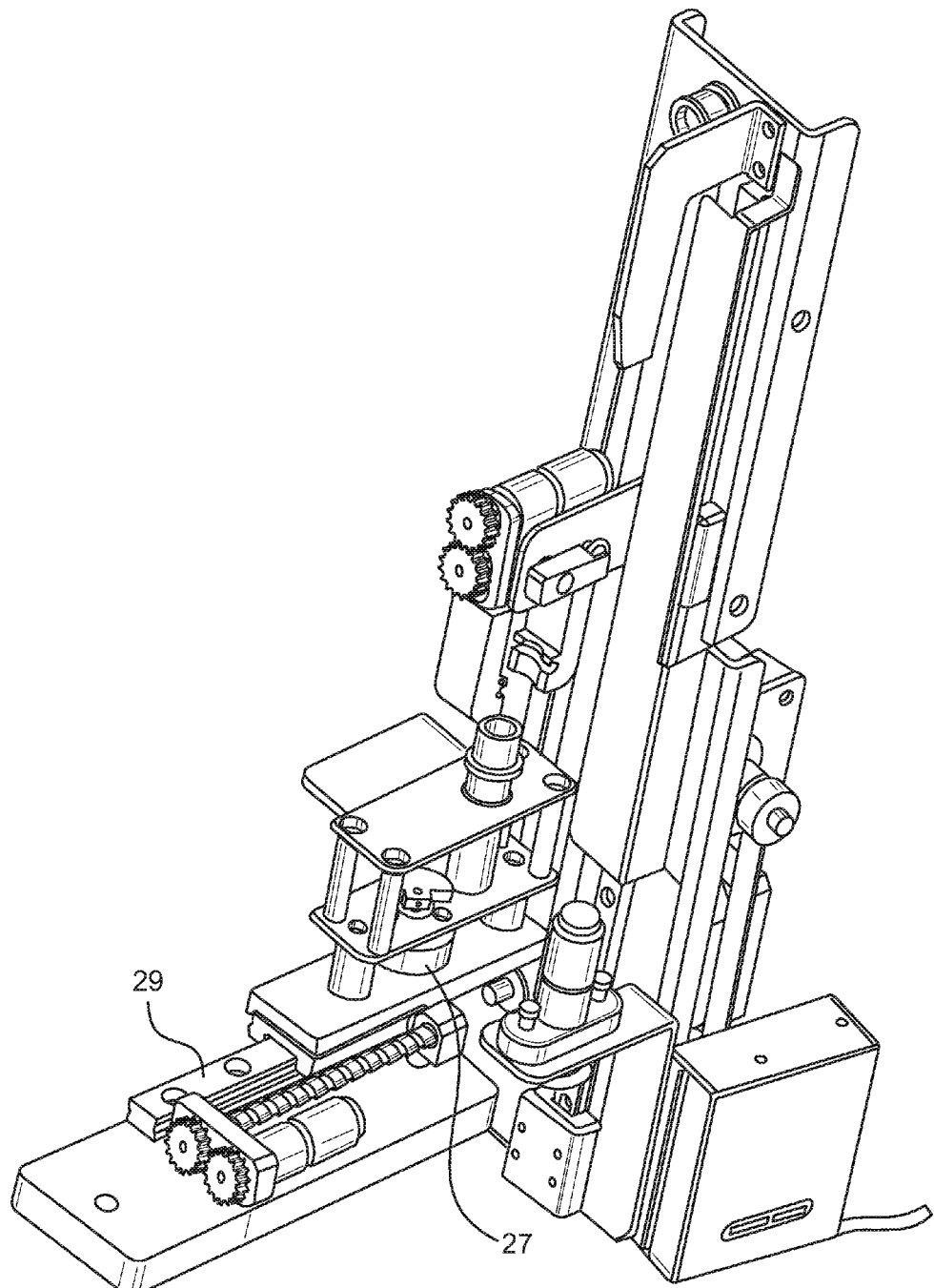
FIG. 4 is a schematic diagram of the shaking device for a fully-automatic instant check meter for shaking peripheral blood vessels under the second state.

By referring to FIG. 1, FIG. 2, FIG. 3 and FIG. 4, a shaking device for a fully-automatic instant check meter is used for shaking blood in a test tube (a vacuum blood vessel 40 or a peripheral blood vessel 50) uniformly, comprising a frame body 1, a barcode printer 2, a first bracket 3, a second bracket 4, a rotating mechanism, a vacuum blood vessel shaking mechanism and a peripheral blood vessel shaking mechanism, wherein a first sliding rail 5, a first motor 6 and a second motor 7 are provided on the frame body 1; the rotating mechanism is connected to the first sliding rail 5 in a sliding manner via a first sliding block 8 and is connected to the first motor 6 via a first synchronous belt 9; the vacuum blood vessel shaking mechanism is connected to the first sliding rail 5 in a sliding manner via a second sliding block 10 and is connected to a second motor 7 via a second synchronous belt 11; the peripheral vessel shaking mechanism is arranged below the vacuum blood vessel shaking mechanism; and the barcode printer 2 is arranged at one side of the frame body 1.

In this embodiment, the rotating mechanism comprises a first bracket 3 and a first DC motor 12. The first bracket 3 is fixed to the first sliding block 8 by screws, and the first DC motor 12 is fixed on the first bracket 3 with the output end downwards. A rotating friction head 13 is arranged on the output end.

In this embodiment, the vacuum blood vessel shaking mechanism comprises a second bracket 4, a guide block 14 and a gripper. The guide block 14 is fixed on the frame body 1 and located above the first sliding rail 5, the second bracket 4 is fixed to the second sliding block 10 by screws. A check block 15 is provided on one side of the second bracket 4, the gripper is connected to the check block 15 via a rotating shaft 16. The check block 15 rotates under the guidance of the guide block 14 and drives the gripper to rotate.

In this embodiment, the gripper comprises a second DC motor 17, a left grab block 18, a right grab block 19 and a first lead screw 20. The second DC motor 17 is fixed on the second bracket 4. The output end of the second DC motor 17 is provided with the first driving wheel 21, and one end of the first lead screw 20 is provided with the first driven wheel 22. The first driving wheel 21 is meshed with the first driven wheel 22, and the left grab block 18 and right grab block 19 are set on the first lead screw 20.

In this embodiment, the peripheral blood vessel shaking mechanism comprises an installation platform 23, a third DC motor 24, a second lead screw 25, a fixed block 26, a brushless motor 27 and a fixing piece 28. The installation platform 23 is provided with a second sliding rail 29, the fixed block 26 is connected with the second sliding rail 29 in a sliding manner. The third DC motor 24 is fixed on the installation platform 23, and the output end of the third DC motor 24 is provided with a second driving wheel 30. One end of the second lead screw 25 is provided with a second driven wheel 31. The second driving wheel 30 is meshed with the second driven wheel 31. The fixed block 26 is connected with the second lead screw 25. The fixing piece 28 is provided with a brushless motor 27. The fixing piece 28 is connected with the fixed block 26 via rubber feet 32. The output end of the brushless motor 27 is provided with an eccentric block 33. A shaking block 34 is arranged above the fixing piece 28, and the shaking block 34 is provided with a jack 35.

In this embodiment, the end of the check block 15 in contact with the guide block 14 is provided with bearings 36.

The shaking device for a fully-automatic instant check meter can shake vacuum blood vessels 40 and peripheral blood vessels 50. Before use of the barcode printer 2, the barcodes on the sample rack are firstly scanned to confirm the type of blood vessels, and then the barcodes on the blood vessels are scanned, to record the barcode information. If the blood vessel on the sample rack is vacuum blood vessel 40 and the barcode of the blood vessel cannot be scanned, the rotating friction head 13 moved downwards to compress the vacuum blood vessels 40 for rotary operation driven by the first motor 6. The vacuum blood vessel shaking mechanism shakes the blood in the vacuum blood vessel 40, and the gripper grips various kinds of blood vessels. The peripheral blood vessel shaking mechanism shakes the blood in the peripheral blood vessel 50; firstly gripping the peripheral blood vessels 50 from the sample rack by the gripper, and then inserting the peripheral blood vessel 50 on the jack 35 of the shaking block 34. The shaking block 34 is driven by the brushless motor 27 to shake, and thus shaking the blood in the peripheral blood vessel 50.

The invention claimed is:

1. A shaking device for a fully-automatic instant check meter is used for shaking blood in vessels, comprising:
    a frame body,
    a barcode printer,
    a first bracket,
    a second bracket,
    a rotating mechanism,
    a first shaking mechanism and a second shaking mechanism,
    wherein a first sliding rail, a first motor and a second motor are provided on the frame body,
    the rotating mechanism is connected to the first sliding rail in a sliding manner via a first sliding block and is connected to the first motor via a first synchronous belt,
    the first shaking mechanism is connected to the first sliding rail in a sliding manner via a second sliding block and is connected to the second motor via a second synchronous belt,
    the second shaking mechanism is arranged below the first shaking mechanism, and the barcode printer is arranged at one side of the frame body;
    wherein the barcode printer scans a barcode on one of the vessels to record information of the barcode;
    wherein a rotating friction head driven by the first motor engages one of said vessels for rotary operation;
    wherein the first and second shaking mechanisms shake selected ones of the vessels for uniformly shaking the blood in the vessels.

2. The shaking device for a fully-automatic instant check meter according to claim 1, wherein the rotating mechanism comprises the first bracket and the first motor, the first bracket is fixed to the first sliding block by screws, and the first motor is fixed on the first bracket with an output end downwards, and the rotating friction head is arranged on the output end, wherein the first motor is a first DC motor.

3. The shaking device for a fully-automatic instant check meter according to claim 2, wherein the first shaking mechanism comprises the second bracket, a guide block and a gripper, the guide block is fixed on the frame body and located above the first sliding rail, the second bracket is fixed to the second sliding rail by screws, a check block is provided on one side of the second bracket, the gripper is connected to the check block via a rotating shaft, the check block rotates under the guidance of the guide block and drives the gripper to rotate.

4. The shaking device for a fully-automatic instant check meter according to claim 3, wherein the gripper comprises a second DC motor, a left grab block, a right grab block and a first lead screw, the second DC motor is fixed on the second bracket, an output end of the second DC motor is provided with a first driving wheel, and one end of the first lead screw is provided with a first driven wheel, the first driving wheel is meshed with the first driven wheel, and the left grab block and right grab block are set on the first lead screw.

5. The shaking device for a fully-automatic instant check meter according to claim 4, wherein the second shaking mechanism comprises an installation platform, a third DC motor, a second lead screw, a fixed block, a brushless motor and a fixing piece, the installation platform is provided with a second sliding rail, the fixed block is connected with the second slide rail in a sliding manner, the third DC motor is fixed on the installation platform, and an output end of the third DC motor is provided with a second driving wheel, one end of the second lead screw is provided with a second driven wheel, the second driving wheel is meshed with the second driven wheel, the fixed block is connected with the second lead screw, the fixing piece is provided with a brushless motor, the fixing piece is connected with the fixed block via rubber feet, an output end of the brushless motor is provided with an eccentric block, a shaking block is arranged above the fixing piece, and the shaking block is provided with a jack.

6. The shaking device for a fully-automatic instant check meter according to claim 3, wherein an end of the check block in contact with the guide block is provided with bearings.

* * * * *